United States Patent
Hafezi et al.

(10) Patent No.: US 8,597,186 B2
(45) Date of Patent: *Dec. 3, 2013

(54) PHARMACEUTICAL DOSAGES DELIVERY SYSTEM

(75) Inventors: Hooman Hafezi, Redwood City, CA (US); Gregory Moon, Orinda, CA (US); Kityee Au-Yeung, San Francisco, CA (US); Robert Duck, San Francisco, CA (US); Maria Casillas Holen, Santa Clara, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 606 days.

This patent is subject to a terminal disclaimer.

(21) Appl. No.: 12/673,150

(22) PCT Filed: Jan. 5, 2010

(86) PCT No.: PCT/US2010/020140
§ 371 (c)(1),
(2), (4) Date: Feb. 11, 2010

(87) PCT Pub. No.: WO2010/080764
PCT Pub. Date: Jul. 15, 2010

(65) Prior Publication Data
US 2011/0306852 A1    Dec. 15, 2011

Related U.S. Application Data

(60) Provisional application No. 61/142,861, filed on Jan. 6, 2009.

(51) Int. Cl.
*A61B 5/07* (2006.01)

(52) U.S. Cl.
USPC .......................................................... 600/302

(58) Field of Classification Search
USPC ............................................. 604/19; 600/302
See application file for complete search history.

(56) References Cited

U.S. PATENT DOCUMENTS

| 3,589,943 A | 6/1971 | Grubb et al. |
| 3,607,788 A | 9/1971 | Adolph |
| 3,642,008 A | 2/1972 | Bolduc |

(Continued)

FOREIGN PATENT DOCUMENTS

| EP | 0344939 | 12/1989 |
| EP | 1246356 | 10/2002 |

(Continued)

OTHER PUBLICATIONS

Bohidar et al., "Dielectric Behavior of Gelatin Solutions and Gels" Colloid Polym Sci (1998) 276:81-86.

(Continued)

*Primary Examiner* — Nicholas Lucchesi
*Assistant Examiner* — Diva K Chander
(74) *Attorney, Agent, or Firm* — Bozicevic, Field & Francis LLP; Bret E. Field

(57) ABSTRACT

Pharmaceutical delivery systems for delivering dosages according to the present invention include a carrier component and a cap configured to seal an internal volume of the carrier component, wherein the cap includes a device that produces a unique current signature. Dosages prepared to be delivered according to embodiments of the invention find use in a variety of different applications, including clinical trials.

26 Claims, 3 Drawing Sheets

(56) References Cited

U.S. PATENT DOCUMENTS

| | | |
|---|---|---|
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,893,111 A | 7/1975 | Cotter |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,494,950 A | 1/1985 | Fischell |
| 4,559,950 A | 12/1985 | Vaughan |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,725,997 A | 2/1988 | Urquhart et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,844,076 A | 7/1989 | Lesho |
| 4,896,261 A | 1/1990 | Nolan |
| 4,975,230 A | 12/1990 | Pinkhasov |
| 4,987,897 A | 1/1991 | Funke |
| 5,016,634 A | 5/1991 | Vock et al. |
| 5,079,006 A | 1/1992 | Urquhart |
| 5,167,626 A * | 12/1992 | Casper et al. ............... 604/891.1 |
| 5,176,626 A | 1/1993 | Soehendra |
| 5,261,402 A | 11/1993 | DiSabito |
| 5,263,481 A | 11/1993 | Axelgaard et al. |
| 5,279,607 A * | 1/1994 | Schentag et al. ........... 604/890.1 |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A * | 3/1995 | D'Andrea et al. ......... 604/890.1 |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,485,841 A | 1/1996 | Watkin et al. |
| 5,567,210 A | 10/1996 | Bates et al. |
| 5,596,302 A | 1/1997 | Mastrocola et al. |
| 5,600,548 A | 2/1997 | Nguyen et al. |
| 5,634,468 A | 6/1997 | Platt |
| 5,645,063 A | 7/1997 | Straka et al. |
| 5,705,189 A | 1/1998 | Lehmann et al. |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,868,136 A | 2/1999 | Fox |
| 5,925,030 A | 7/1999 | Gross et al. |
| 5,957,854 A | 9/1999 | Besson |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,200,265 B1 | 3/2001 | Walsh et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson |
| 6,315,719 B1 | 11/2001 | Rode et al. |
| 6,342,774 B1 | 1/2002 | Kreisinger et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 * | 8/2002 | Raymond et al. ............. 600/300 |
| 6,441,747 B1 | 8/2002 | Khair |
| 6,453,199 B1 * | 9/2002 | Kobozev ......................... 607/40 |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,564,079 B1 | 5/2003 | Cory |
| 6,572,636 B1 | 6/2003 | Hagen et al. |
| 6,577,893 B1 | 6/2003 | Besson |
| 6,579,231 B1 | 6/2003 | Phipps |
| 6,595,929 B2 | 7/2003 | Stivoric |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,800,060 B2 | 10/2004 | Marshall |
| 6,801,137 B2 | 10/2004 | Eggers et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |

(56) References Cited

U.S. PATENT DOCUMENTS

| | | |
|---|---|---|
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 * | 6/2008 | Danowski et al. .......... 340/572.1 |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,616,111 B2 | 11/2009 | Covannon |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,796,043 B2 | 9/2010 | Euliano et al. |
| 7,797,033 B2 * | 9/2010 | D'Andrea et al. ............ 600/424 |
| 7,809,399 B2 | 10/2010 | Lu |
| 7,844,341 B2 | 11/2010 | Von Arx et al. |
| 2001/0027331 A1 | 10/2001 | Thompson |
| 2001/0044588 A1 | 11/2001 | Mault |
| 2001/0051766 A1 | 12/2001 | Gazdzinski |
| 2002/0002326 A1 | 1/2002 | Causey, III |
| 2002/0026111 A1 | 2/2002 | Ackerman |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |

(56) References Cited

U.S. PATENT DOCUMENTS

| | | |
|---|---|---|
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |

(56) References Cited

U.S. PATENT DOCUMENTS

| | | |
|---|---|---|
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1* | 12/2008 | Robertson et al. ............ 600/302 |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1* | 1/2009 | Nunez et al. ................ 340/572.1 |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076343 A1 | 3/2009 | James |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |

(56) References Cited

U.S. PATENT DOCUMENTS

| | | |
|---|---|---|
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0239616 A1 | 9/2010 | Hafezi et al. |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1* | 11/2010 | Hafezi et al. ............ 600/302 |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0105864 A1 | 5/2011 | Robertson et al. |
| 2011/0124983 A1 | 5/2011 | Kroll et al. |
| 2011/0224912 A1 | 9/2011 | Bhavaraju et al. |
| 2011/0230732 A1 | 9/2011 | Edman et al. |
| 2012/0062371 A1 | 3/2012 | Radivojevic et al. |

FOREIGN PATENT DOCUMENTS

| | | |
|---|---|---|
| EP | 1534054 | 5/2005 |
| EP | 1702553 | 9/2006 |
| EP | 1789128 | 5/2007 |
| EP | 2143369 | 1/2010 |
| JP | 61072712 | 4/1986 |
| JP | 05-228128 | 9/1993 |
| JP | 2000-506410 | 5/2000 |
| JP | 2002263185 | 9/2002 |
| JP | 2005-073886 | 3/2005 |
| JP | 2005-087552 | 4/2005 |
| JP | 2005-304880 | 4/2005 |
| JP | 2006006377 | 1/2006 |
| JP | 2006509574 | 3/2006 |
| JP | 2007-313340 | 12/2007 |
| KR | 2006077523 | 7/2006 |
| WO | 8802237 | 4/1988 |
| WO | WO8802237 | 4/1988 |
| WO | WO9221307 | 12/1992 |
| WO | WO9308734 | 5/1993 |
| WO | WO9319667 | 10/1993 |
| WO | WO9739963 | 10/1997 |
| WO | WO9843537 | 10/1998 |
| WO | WO9959465 | 11/1999 |
| WO | WO0033246 | 6/2000 |
| WO | WO 0147466 | 7/2001 |
| WO | WO0174011 | 10/2001 |
| WO | WO0180731 | 11/2001 |
| WO | WO 0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO03068061 | 8/2003 |
| WO | WO 2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004066881 | 8/2004 |
| WO | WO2004109316 | 12/2004 |
| WO | WO2005011237 | 2/2005 |
| WO | WO 2005020023 | 3/2005 |
| WO | WO2005024687 | 3/2005 |
| WO | WO2005047837 | 5/2005 |
| WO | WO2005051166 | 6/2005 |
| WO | WO2005110238 | 11/2005 |
| WO | WO2006021932 | 3/2006 |
| WO | WO2006027586 | 3/2006 |
| WO | WO 2006055892 | 5/2006 |
| WO | WO 2006055956 | 5/2006 |
| WO | WO2006075016 | 7/2006 |
| WO | WO2006100620 | 9/2006 |
| WO | WO 2006116718 | 11/2006 |
| WO | WO 2006127355 | 11/2006 |
| WO | WO 2007001724 | 1/2007 |
| WO | WO 2007001742 | 1/2007 |
| WO | WO 2007013952 | 2/2007 |
| WO | WO 2007014084 | 2/2007 |
| WO | WO2007014527 | 2/2007 |
| WO | WO 2007021496 | 2/2007 |
| WO | WO 2007027660 | 3/2007 |
| WO | WO2007028035 | 3/2007 |
| WO | WO 2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |

(56) References Cited

FOREIGN PATENT DOCUMENTS

| | | |
|---|---|---|
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | WO 2007127316 | 11/2007 |
| WO | WO2007127879 | 11/2007 |
| WO | WO2007127945 | 11/2007 |
| WO | WO2007128165 | 11/2007 |
| WO | WO 2007130491 | 11/2007 |
| WO | WO2007143535 | 12/2007 |
| WO | WO 2007149546 | 12/2007 |
| WO | WO 2006104843 | 1/2008 |
| WO | WO 2008008281 | 1/2008 |
| WO | WO 2008030482 | 3/2008 |
| WO | WO 2008052136 | 5/2008 |
| WO | WO 2008063626 | 5/2008 |
| WO | WO 2008066617 | 6/2008 |
| WO | WO2008076464 | 6/2008 |
| WO | WO2008019683 | 7/2008 |
| WO | WO 2008089232 | 7/2008 |
| WO | WO 2008095183 | 8/2008 |
| WO | WO2008097652 | 8/2008 |
| WO | WO 2008101107 | 8/2008 |
| WO | WO 2008112577 | 9/2008 |
| WO | WO 2008112578 | 9/2008 |
| WO | 2008120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO 2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO 2009146082 | 12/2009 |
| WO | WO2010000085 | 1/2010 |
| WO | WO2010009100 | 1/2010 |
| WO | WO 2010011833 | 1/2010 |
| WO | 2010019778 | 2/2010 |
| WO | 2010057049 | 5/2010 |
| WO | WO2010080765 | 7/2010 |
| WO | WO2010080843 | 7/2010 |
| WO | WO2010107563 | 9/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |

OTHER PUBLICATIONS

Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Given Imaging, "Agile Patency Brochure" (2006) http://www.inclino.no/documents/AgilePatencyBrochure_Global_GMB-0118-01.pdf; 4pp.
ISFET—Ion Sensitive Field-Effect Transistor; Microsens S.A. pdf document. First cited in Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Kamada K., "Electrophoretic deposition assisted by soluble anode" Materials Letters 57 (2003) 2348-2351.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Roulstone, et al., "Studies on Polymer Latex Films: I. A study of latex film morphology" Polymer International 24 (1991) pp. 87-94.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"The SmartPill Wireless Motility Capsule" Smartpill, The Measure of GI Health; (2010) http://www.smartpillcorp.com/index.cfm?pagepath=Products/The_SmartPill_Capsule&id=17814.
Soper, S.A. et al. "Bio-Mems Technologies and Applications", Chapter 12, "MEMS for Drug Delivery", p. 325-346 (2007).
U.S. Appl. No. 12/238,345, filed Sep. 25, 2008, Hooman et al., Non-Final Office Action mailed Jun. 13, 2011 22pp.
Walkey, "MOSFET Structure and Processing"; 97.398* Physical Electronics Lecture 20; First cited in Office Action dated Jun. 13, 2011 for U.S. Appl. No. 12/238,345; 24 pp.
Wongmanerod et al., "Determination of pore size distribution and surface area of thin porous silicon layers by spectroscopic ellipsometry" Applied Surface Science 172 (2001) 117-125.
Gilson, D.R. "Molecular dynamics simulation of dipole interactions", Department of Physics, Hull University, Dec. 2002, p. 1-43.
Li, P-Y, et al. "An electrochemical intraocular drug delivery device", Sensors and Actuators A 143 (2008) p. 41-48.
NPL_AntennaBasics.pdf, p. 1-3.
Santini, J.T. et al, "Microchips as controlled drug delivery-devices", Agnew. Chem. Int. Ed. 2000, vol. 39, p. 2396-2407.
Shawgo, R.S. et al. "BioMEMS from drug delivery", Current Opinion in Solid State and Material Science 6 (2002), p. 329-334.
Soper, S.A. et al. "Bio-Mems Technologies and Applications", Chapter 12, "MEMS for Drug Delivery", p. 325-346.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Arshak et al., A Review and Adaptation of Methods of Object Tracking to Telemetry Capsules IC-Med (2007) vol. 1, No. 1, Issue 1, pp. 35 of 46.
"ASGE Technology Status Evaluation Report: wireless capsule endoscopy" American Soc. For Gastrointestinal Endoscopy (2006) vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Brock, "Smart Medicine: The Application of Auto-ID Technology to Healthcare" Auto-ID Labs (2002) http://www.autoidlabs.org/uploads/media/MIT-AUTOID-WH-010.pdf.

(56) References Cited

OTHER PUBLICATIONS

Carlson et al., "Evaluation of a non-invasive respiratory monitoring system for sleeping subjects" Physiological Measurement (1999) 20(1): 53.
Delvaux et al., "Capsule endoscopy: Technique and indications" Clinical Gastoenterology (2008) vol. 22, Issue 5, pp. 813-837.
Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.
Given Imaging, "Agile Patency Brochure" http://www.inclino.no/documents/AgilePatencyBrochure_Global_GMB-0118-01.pdf;(N.D.) 4pp.
Gonzalez-Guillaumin et al., "Ingestible capsule for impedance and pH monitoring in the esophagus" IEEE Trans Biomed Eng. (2007) 54(12: 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Heydari et al., "Analysis of the PLL jitter due to power/ground and substrate noise"; IEEE Transactions on Circuits and Systems (2004) 51(12): 2404-16.
INTROMEDIC, MicroCam Innovative Capsule Endoscope Pamphlet. 8 pp (http://www.intromedic.com/en/product/productinfo.asp).
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
MacKay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Melanson, "Walkers swallow RFID pills for science" Engadget (2008); http://www.engadget.com/2008/07/29/walkers-swallow-rfid-pills-for-science/.
Minimitter Co. Inc. "Actiheart" Traditional 510(k) Summary. Sep. 27, 2005.
Minimitter Co. Inc. Noninvasive technology to help your studies succeed. MiniMitter.com Mar. 31, 2009.
Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
Minimitter Co. Inc. VitalSense Integrated Physiological Monitoring System. Product Description.
Minimitter Co. Inc. VitalSense Wireless Vital Signs Monitoring. Temperatures.com Mar. 31, 2009.
Mohaverian et al., "Estimation of gastric residence time of the Heidelberg capsule in humans: effect of varying food composition" Gastroenterology (1985) 89:(2): 392-7.
"New 'smart pill' to track adherence" E-Health-Insider (2010) http://www.e-health-insider.com/news/5910/new_'smart_pill'_monitors_medicines.
Philips Respironics (http/minimitter.com/products.cfm) Products, Noninvasive Technology to Help Your Studies Succeed. 510(k) Permanent Notification for Vital Sense. Apr. 22, 2004.
"RFID "pill" monitors marchers" RFID News (2008) http://www.rfidnews.org/2008/07/23/rfid-pill-monitors-marchers/.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
"SensiVida minimally invasive clinical systems" Investor Presentation Oct. 2009 28pp; http://www.sensividamedtech.com/SensiVidaGeneralOctober09.pdf.
Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.
"The SmartPill Wireless Motility Capsule" Smartpill, The Measure of GI Health; http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Swedberg, "University Team Sees Ingestible RFID Tag as a Boon to Clinical Trials" RFID Journal Apr. 27, 2010; http://www.rfidjournal.com/article/view/7560/1.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
University of Florida News "Rx for health: Engineers design pill that signals it has been swallowed" (2010) 2pp.; http://news.ufl.edu/2010/03/31/antenna-pill-2/.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
Gaglani S. "Put Your Phone, or Skin, on Vibrate" MedGadget (2012) http://medgadget.com/2012/03/put-your-phone-or-skin-on-vibrate.html 8pp.
Rolison et al., "Electrically conductive oxide aerogels: new materials in electrochemistry" J. Mater. Chem. (2001) 1, 963-980.
ISFET—Ion Sensitive Field-Effect Transistor; Microsens S.A. pdf document. pp. 1-4.
Walkey, "MOSFET Struture and Processing"; 97.398* Physical Electronics Lecture 20; pp. 1-24.
Coury, L. "Conductance Measurement Part 1: Theory"; Current Separations, 18:3 (1999) p. 91-96.
Watson, et al., "Determination of the relationship between the pH and conductivity of gastric juice" Physiol Meas. 17 (1996) pp. 21-27.
"Smartlife awarded patent for knitted transducer" Innovation in Textiles News: http://www.innovationintextiles.com/articles/208.php; 2pp. (2009).
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

\* cited by examiner

PHARMACEUTICAL DOSAGES DELIVERY SYSTEM

CROSS-REFERENCE

Pursuant to 35 U.S.C. §119 (e), this application claims priority to the filing date of U.S. Provisional Patent Application Ser. No. 61/142,861 filed on Jan. 6, 2009, the disclosure of which application is herein incorporated by reference. This application also claims the benefit of PCT Application No. PCT/US10/20140 of the same title filed on Jan. 5, 2010, which is herein incorporated by reference.

FIELD OF THE INVENTION

This invention relates generally to electronic devices and, more specifically, to electronic devices that are part of a communication system that uses conduction to communicate information.

INTRODUCTION

Prescription medications are effective remedies for many patients when taken properly. However, studies show that on average, about 50% of patients do not comply with prescribed medication regimens. A low rate of adherence with medication regimens results in a large number of hospitalizations and admissions to nursing homes every year. In the United States alone, it has recently been estimated that costs resulting from patient non-adherence amount to over $100 billion annually.

One situation where patient adherence is of particular importance is in the context of clinical studies. Non-adherence in the clinical trial setting has long-range consequences far beyond the few hundred patients who might be involved in a trial. To the extent that non-adherence occurs without a correction factor, it may have effects ranging from failure to gain FDA approval to the necessity for increasing the recommended dose beyond that which would be required of a fully compliant population. Such an elevated dose could cause a higher incidence of side effects, which in turn may lead to further non-adherence.

Clinical studies typically enroll patients to undergo specific drug treatment regimens with the goal of testing hypotheses related to the effects of drug treatment on medically relevant clinical endpoints. Such studies might measure, for example, the relationship between alternative drug treatments with any of a wide variety of clinical endpoints, ranging from physiological, biochemical or psychological measurements, to manifestations of disease, patient survival or quality of life. In addition, drug treatments must also be related to any observed adverse events in an effort to identify rare adverse reactions or interactions with other medications.

The ability to reliably correlate highly specific drug treatment regimens, including dosage and administration methods, with both efficacy and safety depends to a great extent on the certainty of knowledge that every patient has followed the prescribed treatment regimen. Monitoring of patient adherence, including the exact time of administration for medications, is therefore of great value to clinical trial sponsors as well as the pharmaceutical industry in general.

Therefore, what is needed is a system and method for tracking the dosage administered and the time timing of the administration.

SUMMARY

Devices of the invention include a carrier component and a cap configured to seal an internal volume of the carrier component, where the cap includes a communication device that encodes information in current flow. The device includes an ingestible event marker or an ionic emission module identifier that use conduction through conducting fluid in contact with the device. Devices of invention find use in preparing a pharmaceutical dosage. Additional aspects of the invention include dosages prepared in accordance with the methods of the invention. Dosages prepared according to embodiments of the invention find use in a variety of different applications, including clinical trials.

DETAILED DESCRIPTION

Figure 1A:
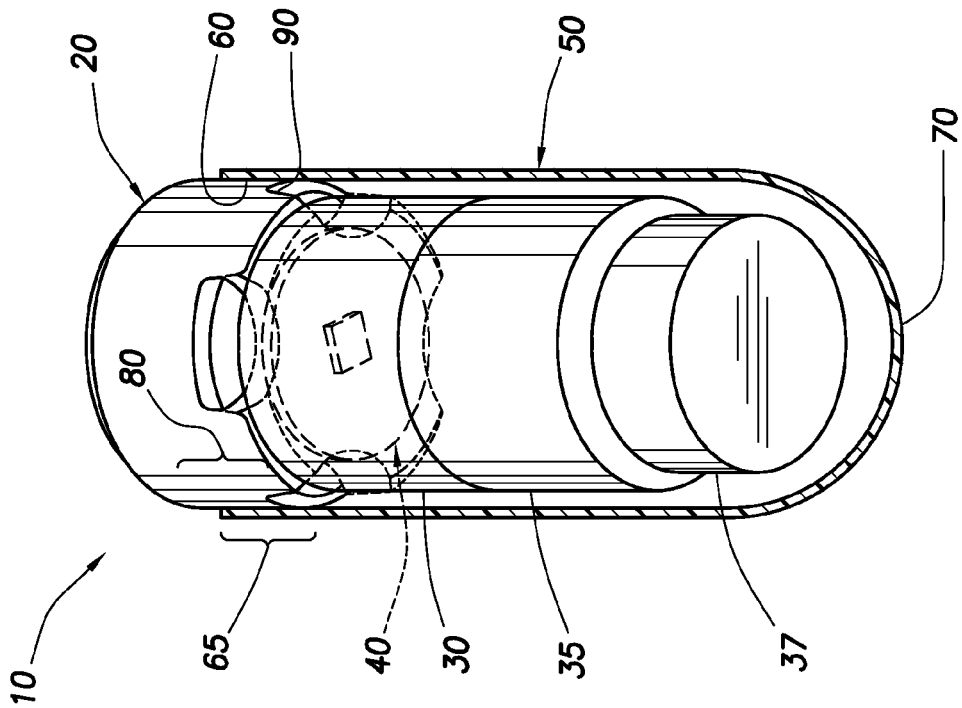
FIG. 1A provides a partial cut-away and perspective front view of a pharmaceutical dosage delivery system according to the present invention with a current signature producing device positioned on the exterior of the delivery system.

Devices of the invention include a carrier component and a cap configured to seal an internal volume of the carrier component, where the cap includes an ingestible event marker identifier. Devices of invention find use in preparing a pharmaceutical dosage. Additional aspects of the invention include dosages prepared in accordance with the methods of the invention. Dosages prepared according to various aspects of the invention find use in a variety of different applications, including clinical trials.

In describing the invention in greater detail, devices of the invention and methods for their use in preparing a pharmaceutical dosage are reviewed first, followed by a discussion of the utility of such methods, and assemblies and systems involving the same. Also reviewed in greater detail below are kits for practicing methods of the invention.

As summarized above, devices and methods for their use in preparing pharmaceutical dosages are provided. The term "pharmaceutical dosage" refers to a physically discrete structure that contains a known amount of active agent, where the known amount of active agent is one that has been selected for administration to a subject at an active agent administration event. A pharmaceutical dosage therefore contains a predetermined quantity of a pharmaceutically active agent (also referred to herein simply as an "active agent"). The amount of pharmaceutically active agent that is present in the pharmaceutical dosage is calculated to be sufficient to produce a desired effect when administered to a subject at an active agent administration event. A pharmaceutical dosage produced by methods of the invention may have any of a variety of different configurations. As such, the pharmaceutical dosage may be cylindrical, spherical or elliptical in shape, or any other convenient shape. Of interest are pharmaceutical dosages that have a substantially capsule configuration, as reviewed in greater detail below.

Devices of the invention include a carrier component and a cap configured to seal an internal volume of the carrier component, where the cap includes an ingestible event marker identifier. These components of the devices may vary, where different aspects of these components are described in greater detail below.

Methods of the invention include filling a carrier component with a pharmaceutically active agent composition and then sealing the carrier component with a cap to produce the pharmaceutical dosage. The carrier component is a container that holds an amount of pharmaceutically active agent composition. Depending on the particular nature of the pharmaceutically active agent composition (described in greater detail below), the carrier component may be configured to hold a variety of types of compositions, including liquids and solids, such as powders, tablets, coated particulate compositions, pellets, beads and spherules. While the volume of the active agent that the carrier is configured to hold may vary, in some instances the carrier may be configured to a quantity of active agent ranging from 0 to 1 g, such as 0 to 100 mg and including 0 to 5 mg. The carrier component may have a variety of different configurations. Examples of carrier component configurations include, but are not limited to partial box shapes, partial spherical shapes, partial ovoid shapes, partial conical shapes, etc.

One carrier component configuration of interest is a partial-capsule configuration. Partial-capsule configurations are those configurations having a first, open end and a second, closed end, where the open and closed ends are separated by a distance sufficient to provide a desired internal volume to the carrier component. Partial-capsule configurations finding use may have a variety of different cross-sectional configurations, where the cross-sectional configuration is the shape defined by the walls of the carrier component at the open end. Cross-sectional configurations of interest include, but are not limited to circular, rectangular, triangular, square and oval, as well as irregular cross sectional configurations.

Partial-capsule configured carrier components of the invention may have varied dimensions, as desired. In some instances, the length of the carrier component ranges from 1 mm to 50 mm, such as 5 mm to 30 mm and including 10 mm to 20 mm. The outer diameter of the carrier component may vary, ranging in some instances from 1 mm to 30 mm, such as 5 mm to 20 mm and including 5 mm to 10 mm. The inner diameter of the carrier component may also vary, ranging from 0.5 mm to 29.99 mm, such as 3.0 mm to 19.99 mm and including 3.0 mm to 9.99 mm. The walls of the carrier component may vary, so long as they are sufficiently thick to hold the pharmaceutically active agent composition, where in some instances the walls range in thickness from 0.01 mm to 2 mm, such as 0.01 mm to 0.2 mm and including 0.01 mm to 0.1 mm. The dimensions may be constant or variable in the carrier component, as desired. For example, the inner diameter may be constant along the length of the capsule or may vary.

Carrier components of the invention, such as partial-capsule configured carrier components, may be fabricated from any convenient material using any convenient protocol. Materials of interest from which the carrier components may be fabricated include physiologically acceptable polymeric materials that are used in conventional pharmaceutical capsule dosages. The materials may be clear or opaque, and may be colored as desired. Of interest are both rigid and elastic materials.

Suitable polymers from which carrier components of the invention may be fabricated include, but are not limited to: gelatins, polyvinyl alcohol (PVA); natural and synthetic polysaccharides, including pullulan, carrageenan, xanthan, chitosan agar gums, and cellulosic materials, such as carboxymethylcellulose, hydroxypropylmethylcellulose (HPMC), methylcellulose, hydroxyethylcellulose, hydroxyethyl methylcellulose, hydroxypropylcellulose; polyethylene glycols (PEGs), polyethylene oxides (PEOs), mixtures of PEGs and PEOs; acrylic and methacrylic acid based polymers, such as EUDRAGIT E™, EUDRAGIT L™ and/or EUDRAGIT S™ methacrylic acid polymers), EUDRAGIT RL™ and/or EUDRAGIT RS™ ammonium methacrylate copolymers; povidone (polyvinyl pyrrolidone), polyglycolysed glycerides (such as GELUCIRE 44/14™, GELUCIRE 50/02™, GELUCIRE 50/13™ and GELUCIRE 53/10™ polymers); carboxyvinyl polymers (such as CARBOPOL™ polymers); polyoxyethylene-polyoxypropylene copolymers (such as POLOXAMER188™ polymer); and the like.

The surface of the carrier component may be smooth or comprised of variegations and/or grooves arranged in any pattern. Where desired, the carrier component has compartments or partitions. The carrier component may have multiple compartments, such that each compartment has different active agent release characteristics, or contains a different pharmaceutically active agent composition, for example as described in U.S. Pat. Nos. 4,738,724; 5,672,359 and 5,443,461; the disclosures of which applications are herein incorporated by reference.

The carrier components may be fabricated using any convenient protocol, including molding, etc. Fabrication protocols of interest include, but are not limited to, those described in U.S. Pat. Nos. 5,705,189; 4,576,284; 4,591,475; 4,655,840; 4,738,724; 4,738,817 and 4,790,881; the disclosures of which are herein incorporated by reference. Alternatively, the carrier component may be obtained from a commercial vendor, such as Qualicaps Inc., Whitsett N.C.

In methods of the invention, the carrier component may be filled with a variety of different types of pharmaceutically active agent compositions. The protocol that is employed to fill the carrier component may vary depending on the nature of the pharmaceutically active agent composition. For example, flowable compositions such as liquids and solids (particulate and spherule compositions being examples of flowable solids) may be poured into the internal space of the carrier component, either manually, using an automated device, or a combination thereof, in order to fill the carrier component with the pharmaceutically active agent composition. Non-flowable solids, such as tablets or capsules, may be positioned inside of the internal volume of the carrier component, again either manually, using an automated device, or a combination thereof, in order to fill the carrier component.

As indicated above, the pharmaceutically active agent compositions may be solid or liquid compositions. Solid compositions of interest include, but are not limited to: powders, pellets, e.g., in the form of beads or spherules, coated granules and tablets. Liquid compositions of interest may vary, for example in terms of viscosity, color, etc. Pharmaceutically active agent compositions of the invention include a pharmaceutically active agent, either alone or in combination with a vehicle, where the vehicle may include one or more different components, such as fillers, binders, coloring agents, etc.

As used herein, the term "active agent" includes any compound that produces a physiological result, for example a beneficial or useful result, upon contact with a living organism, such as a human. Active agents are distinguishable from such vehicle components such as fillers, binders, coloring agents, etc. The active agent may be any molecule that is capable of modulating a biological process in a living subject. In some instances, the active agent may be a substance used in the diagnosis, treatment, or prevention of a disease or as a component of a medication. Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc. Active agents of interest are further disclosed in PCT Application Serial No. US2006/016370 published as WO 2006/116718, the disclosure of which is herein incorporated by reference.

The pharmaceutically active agent composition may further include a vehicle component, as mentioned above. Vehicle components may include one or more constituents, including but not limited to fillers, binders, disintegrants, coloring agents, etc. Vehicle components of interest are further reviewed in PCT Application Serial No. US2006/016370 published as WO 2006/116718, the disclosure of which is herein incorporated by reference. Additional disclosure of components that can be present in compositions of the invention can be found in Remington's Pharmaceutical Sciences, Mace Publishing Company, Philadelphia, Pa., 17th ed. (1985).

In some instances, the methods may include providing a filler composition that is separate from the active agent composition in the carrier component. For example, in some instances the carrier component is filled with both a pharmaceutically active agent composition and a distinct filler composition, where the filler composition may be included for a variety of different purposes. One type of filler composition of interest is one that imparts to the pharmaceutical dosage composition a density that is greater than stomach fluid. Accordingly, filler compositions of interest are ones that impart to the pharmaceutical dosage composition a density that is 0.8 or greater, such as 1.0 or greater and including 1.2 or greater. Any convenient material may be employed as a filler composition, including the materials described as vehicle components, above.

The filler may also be included to fill any void space present when a device or identifier, such as an ingestible event marker (IEM, which is also known as an ionic emission module) identifier is placed inside of the carrier components. The identifier component of the dosages provides for a number of advantages. The presence of the identifier allows one to monitor the exact time and frequency of medication administration, as well as patient response. This information obtainable by use of the methods and dosages of the invention can be exploited in a number of settings, such as, for example, in improving the overall quality and accuracy of clinical studies. Using such information, one can readily identify members of the clinical trial who comply with a treatment regimen and exclude those that do not in order to obtain more accurate data regarding efficacy of a given active agent. Such information can also be combined with various types of physiological data in order to obtain more comprehensive information regarding the effect of a given active agent.

The methods of the invention also find use with pharmacists, who can prepare patient customized dosages that include an IEM, even if the original manufacturers of the active agent of interest does not provide dosages that include an IEM. An IEM is a device that is dimensioned to be ingestible and includes a conductance control module and a partial power source that is completed upon contact with conducting fluid. As the IEMs are dimensioned to be ingestible, they are sized so that they can be placed in a human mouth and swallowed. In some instances, IEMs of the invention have a longest dimension that is 30 mm or less, such as 20 mm or less, including 5 mm or less. As such, any pharmaceutical composition currently available can be associated with an IEM using methods and components of the invention.

Following placement of the pharmaceutically active agent composition (and any optional filler composition as desired) into the internal volume of the carrier component, the resultant filled carrier component is then sealed with a cap. A cap is a structure configured to mate with the open end of a carrier component in a sealing relationship, such that when the cap is associated with the open end of the carrier component, an internal volume of the carrier component and contents thereof (the pharmaceutically active agent composition) are sealed from the external environment of the dosage structure defined by the carrier and cap, such that gases and liquids may not readily pass between the external and internal environments of the dosage structure. The cap may be fabricated from any suitable material, including the materials described above in connection with the carrier component. In some instances, the cap is fabricated from microcrystalline cellulose, croscarmellose sodium and magnesium stearate.

Caps of the invention include one or more IEM identifiers. The one or more IEM may be present at a variety of different locations of the cap, including internal locations and external locations. Internal locations include areas defined inside of the cap that are configured to receive the IEM. External locations include outer and inner surfaces. Outer surfaces of the cap are those surfaces that face the external environment of the cap when the cap is in a sealing relationship with the carrier component. The outer surface may be a side surface of the cap or a top surface of the cap, as desired. Inner surfaces of the cap are those surfaces that face the internal volume defined by the carrier component and cap when the cap is in a sealing relationship with the carrier component. A given cap may include a single IEM or two or more IEMs, such as three or more ingestible event markers.

The one or more IEMs are stably associated with the cap. As such, the identifiers are fixed to a location of the cap, such as an outer surface of the cap, for example by use of an adhesive. Adhesives of interest include, but are not limited to: sugar and cellulosic adhesives, protein adhesives such as zein or casein, silicone adhesives, polymeric adhesives, including acrylic and methacyrlic adhesives, shellac, and the like.

IEMs of interest are identifiers that communicate information through production of a unique current signature that flows through a conducting environment, such as a conducting fluid, upon contact of the IEM with a target physiological location (or locations). The IEMs may vary depending on the particular embodiment and intended application of the composition, as long as they are activated (turned on) upon contact with a target physiological location, such as the stomach fluid or intestinal fluid. As such, an IEM may be an identifier that produces a unique current signature encoded with information when activated at a target site, for example when the IEM contacts a target body site. The IEM may be any component or device that is capable of providing a detectable signal following activation. IEMs according to various aspects of the present invention comprise a control unit for producing a unique current signature. The IEM may be configured to produce the unique current signature once the composition comes into contact with a physiological target site. Depending on the embodiment, the target physiological site or location may vary, where representative target physiological sites of interest include, but are not limited to: a location in the gastrointestinal tract, such as the mouth, esophagus, stomach, small intestine, large intestine, etc. IEMs may be configured to be activated upon contact with fluid at the target site, e.g., stomach fluid, regardless of the particular composition of the target site. Where desired, the identifier may be configured to be activated by interrogation, following contact of the composition with a target physiological site. The IEM may be configured to be activated after a specific period of time, wherein the target site is reached after a specified period of time.

Depending on the needs of a particular application, the information obtained from the IEM may be generic, such that the information merely identifies that the composition has contacted the target site. Alternatively, the information may be unique, which in some way uniquely identifies that a particular IEM from a group or plurality of different markers in a batch of dosages has contacted a target physiological site. As such, the IEM may be one that, when employed with a batch of dosages, emits a current signature which cannot be distinguished from the current signature emitted by the IEM of any other dosage member of the batch. Alternatively, each IEM of the batch may emit a unique signal, at least with respect to all the other IEMs of the batch. In these instances, each IEM of the batch produces a current signature that uniquely identifies that particular IEM with respect to all other IEMs in the batch. The IEM may emit a unique current signature that is a universally unique current signature (where such a current signature may be analogous to a human fingerprint which is distinct from any other fingerprint of any other individual and therefore uniquely identifies an individual on a universal level). The current signature may either directly convey information about a given event, or provide an identifying code, which may be used to retrieve information about the event from a database, i.e., a database linking identifying codes with compositions.

The duration of the current generation period of the IEM may vary, in accordance with the teachings of the present invention, from 0.1 μsec to 48 hours or longer, such as from 0.1 μsec to 24 hours or longer, such as from 0.1 μsec to 4 hours or longer, such as from 1 sec to 4 hours, including from 1 minute to 10 minutes. Depending on the given embodiment, the IEM may produce the same information encoded in the current signature one time; alternatively, the IEM may be configured to produce the current signature with the same information (identical), two or more times, where the collection of discrete identical current signatures may be collectively referred to as a redundant signal.

In addition to producing a unique current signature, in accordance with other aspects of the present invention, the IEM may be configured to generate a variety of different types of signals, including but not limited to: RF signals, magnetic signals, acoustic signals, etc.

The IEM may vary depending on the particular embodiment and intended application of the composition so long as they are activated (i.e., turned on) upon contact with a target physiological location, such as the stomach. The IEM includes a partial power source that is completed by a conducting fluid, such as stomach acid, and a conductance control unit. Examples of different types of IEMs of interest include, but are not limited to, those described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753; and U.S. patent application Ser. No. 12/564,017 filed Sep. 21, 2009, the disclosures of which are herein incorporated by reference.

The cap may have a variety of different configurations so long as it is configured to seal the open end of the carrier component when it is associated with the open end of the carrier component. The cap may have a variety of different configurations which allow it to seal the open end of the carrier component when associated with the open end of the carrier component. In some instances, the cap has interlocking elements which operate in conjunction with mating elements of the open end of the carrier component to seal the open end of the carrier component. Examples of interlocking elements are screw threads and snap-fit elements. Alternatively, the cap may have a region or end that is configured to pressure fit inside of the carrier component and seal the contents of the carrier component. An example of such a configuration is where the cap has an end made up of a rigid material, where the configuration of the end is slightly larger than the open end of the carrier component. Where the open end of the carrier component is made of an elastomeric material, the rigid end of the cap can be pressure fit into the open end of the carrier by stretching the open end of the carrier. When any stretching force is removed from the open end of the carrier, the open end of the carrier will then comply with the rigid end of the cap in a sealing relationship. Alternatively, the cap may include a compressible end which has a certain amount of compliancy. This compliancy is sufficient to impart to the cap the ability to pressure fit the pliable end of the cap inside the open end of the carrier component by compressing the compressible end to produce a compressed end, placing the compressed end of the cap in the open end of the carrier component and then removing the compressive force. When the compressed end expands as a result of removal of the compressive force, the compressed end conforms to the configuration of the open end of the carrier component in a sealing relationship to seal the contents of the carrier component inside of the carrier component.

A cap with a compressible end can be provided in a number of different ways. One type of compressible end is an end that is fabricated from a compressible material. Compressible materials of interest are pliable. Alternatively, the compressible end may include one or more cut-outs that impart compressibility to the compressible end.

Where desired, the cap may be secured to the open end of the carrier component with an adhesive, where examples of suitable adhesives are provided above. As such, the cap may be glued onto the open end of the carrier component in order to seal the open end of the carrier component.

In some instances, passageways or analogous structures are provided in the carrier and/or cap which facilitate liquid penetration of the dosage form, dissolution of the carrier components and/or reduce buoyancy of the dosage form. When present, such holes may range from $10^{-3}$ to 5 mm in diameter, such as 0.1 to 2 mm in diameter.

Figure 2B:
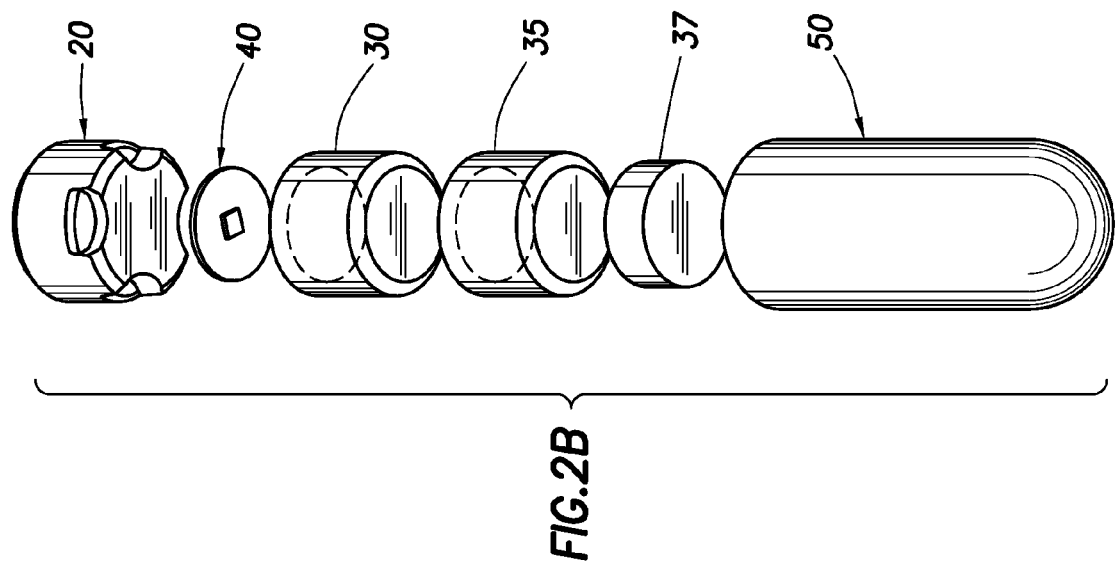
FIG. 2B provides an exploded perspective view of the pharmaceutical dosage delivery system of FIG. 1B.
Figure 2A:
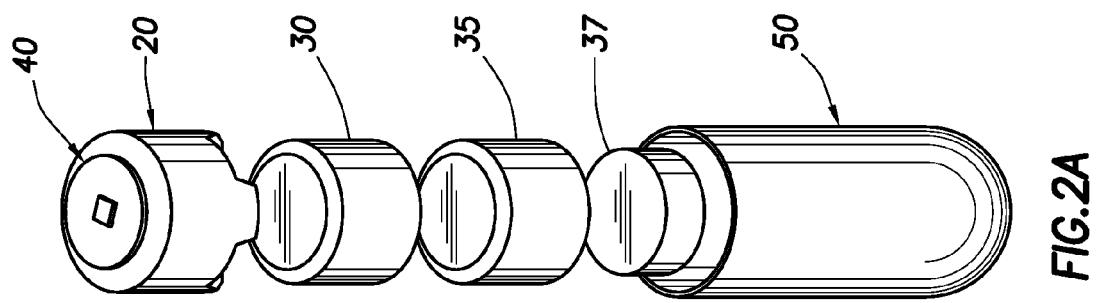
FIG. 2A provides an exploded perspective view of the pharmaceutical dosage delivery system of FIG. 1A.

Referring now to FIGS. 1A and 2A, a pharmaceutical dosage carrier system 10 includes a cap 20 and housing or housing 50. The housing 50 of the system 10 defines a cavity and includes an open end 60 and a closed end 70. The closed end 70 has a partially-planer base with side walls extending from the base in an upward direction, finishing with an open mouth at the open end 60 to define the cavity therein. The closed end 70 may also be a rounded structure, such as a hemispherical end wall, among other configurations, and have a conical configuration, etc.

The system 10 includes an engagement area 65 on the inner wall of the housing 50. The engagement area 65 can be engaged with the cap 20 when the cap 20 is inserted into the open end 60 of the housing 50 in a manner sufficient to produce a seal between the housing 50 and the cap 20. The cap 20 and housing 50 sizes are chosen such that there is contact between the external wall of the cap 20 and the internal wall of the engagement area 65 of the housing 50.

Figure 1B:
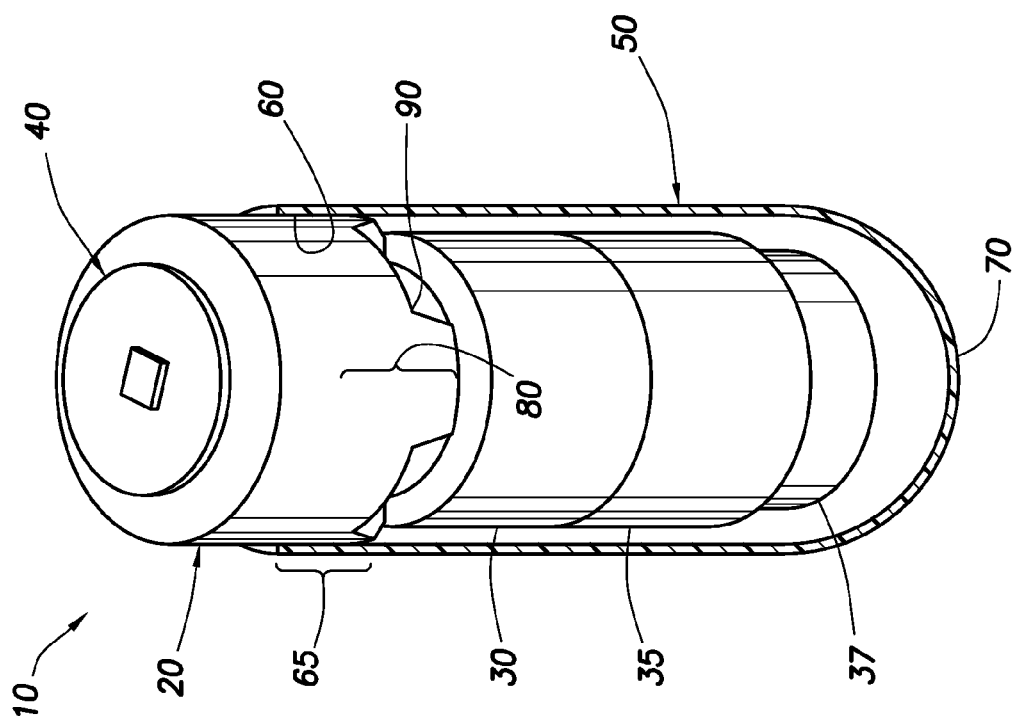
FIG. 1B provides a partial cut-away and perspective front view of a pharmaceutical dosage delivery system according to the present invention with a current signature producing device positioned on the interior of the delivery system.

As reviewed above, the system 10 may be filled with a pharmaceutically active agent composition and/or a filler composition. In accordance with one aspect of the present invention, the system 10 is filled with a pharmaceutically active agent composition and two filler compositions that are in the form of tablets. As such, the housing 50 is filled with a pharmaceutically active agent tablet 30 and two filler compositions 35 and 37. Although shown in a specific order within the cavity defined by the housing 50, the scope of the present invention is not limited by the relative positions or the order of the tablet 30 and the filler compositions 35 and 37. For example, the tablet 30 may be positioned at the location of filler composition 37 as shown in FIG. 1A. Additionally, the orientation of the tablet 30 and the filler composition 35 and 37 may be flipped to better accommodate assembly of the system 10, as shown in FIGS. 1B and 2B, and the scope of the present invention is not limited thereby. At least one of the filler compositions 35 and 37 are fabricated from a material such that impart a density to the overall system 10. In accordance with one aspect of the present invention, the density may be greater than the density of the environment that the system 10 enters or is introduced to, such as stomach fluid. Thus, either one of the filler compositions 35 and 37 can be used to alter the buoyancy of the system 10; the other filler composition may be used to prevent movement of the tablet 30 and the other filler composition within the cavity defined by the housing 50. In accordance with another aspect of the present invention, both of the filler compositions may be used to alter the buoyancy of the system 10. In accordance with the teaching of the present invention, either one of filler compositions may be replaced by a pharmaceutical agent, such that the system 10 includes two (or more?) different pharmaceutically active agents that are released into the surrounding environment at different times or at the same times.

Referring now to FIGS. 1A and 1B, in assembling the system 10, the pharmaceutically active agent, such as the tablet 30, and the two filler compositions 35 and 37 are positioned inside of housing 50 as shown. This positioning step may be accomplished manually or by automatic methods, such as through the use of an assembly machine, remote robot, or other automated device. Following placement of the tablet 30 and the filler compositions 35 and 37 into the housing 50, the open end 60 of the housing 50 is sealed with the cap 20 to seal the system 10. Sealing the open end 60 of the housing 50 with the cap 20 may be accomplished manually or by automatic methods, such as through the use of an assembly machine, remote robot, or other automated device.

As shown in FIGS. 1A and 2A, the cavity defined by the housing 50 that contains the tablet 30 as well as the filler compositions 35 and 37 is sealed with the cap 20. The cap 20 may be pressure-fit inside of the open end 60 of the housing 50. In accordance with another aspect of the present invention, the cap 20 may be glued to the engagement area 65.

Referring now to FIGS. 1A and 2A, the cap 20 includes a device 40, such as an IEM, on a top-outer surface thereof. The device 40 is secured to the upper surface of the cap 20 through the use of a suitable securing method. For example, in accordance with one aspect of the present invention the device 40 is glued to the cap 20 using a suitable adhesive. Alternatively, as shown in FIGS. 1B and 2B, the device 40 maybe secured to a bottom-inner surface of the cap 20 such that when the cap 20 is positioned within the cavity of the housing 50, the device 40 is sealed therein and protected from contact with the surrounding environment that the system 10 is introduced to until the cap 20 is released from the housing 50.

In accordance with another aspect of the present invention, the device 40 includes a virtual dipole element as described in PCT application serial no. PCT/US2008/077753; the disclosure of which application is herein incorporated by reference. In accordance with other aspect of the present invention, the device 40 may not be visible.

Referring now to FIGS. 1A and 2A, the cap 20 includes an insertion portion 80 that is fitted into the open end 60 of the housing 50, as described above. The insertion portion 80 is opposite the surface on which the device 40 is positioned. As shown, the insertion portion 80 defines at least one cut-out portion 90 that allows the insertion portion 80 to be fitted inside of the open end 60. The open end 60 may be malleable to stretch over and pressure fit onto the insertion portion 80 and provide for a secure fit. As such, the cap 20 may be pinched to fit into the open end 60 of the housing 50 when used to seal the insertion portion 80 into the open end 60.

Referring now to FIGS. 1B and 2B, the cap 20 includes an insertion portion 80 that is fitted into the open end 60 of the housing 50, as described above. The insertion portion 80 is located proximal to the bottom surface of the cap 20. The bottom surface of the cap 20 is shaped to receive the device 40 that is positioned on and secured to the bottom surface. As shown, the insertion portion 80 defines a plurality of cut-out portions 90 that allows the insertion portion 80 to be fitted inside of the open end 60. However, the scope of the present invention is not limited by the shape or the number of cut-out portions on the bottom surface of the cap 20. The open end 60 may be malleable to stretch over and pressure fit onto the insertion portion 80 and provide for a secure fit. Alternatively and in accordance with another aspect of the present invention, the open end 60 may be rigid and tapered (not shown) to matingly receive a tapered insertion portion (not shown) of the cap 20, wherein the tapered portion or the open end 60 and the tapered insertion portion of the cap 20 are glued together. As such, the cap 20 may be pressed and glued into the open end 60 of the housing 50 to secure the cap 20 to housing 50.

Figure 3A:
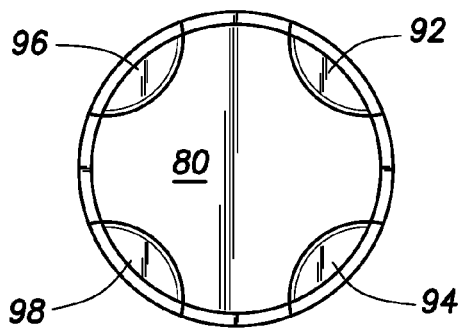
FIG. 3A provides a bottom view of a cap used in the pharmaceutical dosage of FIG. 1 in accordance with the present invention.
Figure 3C:
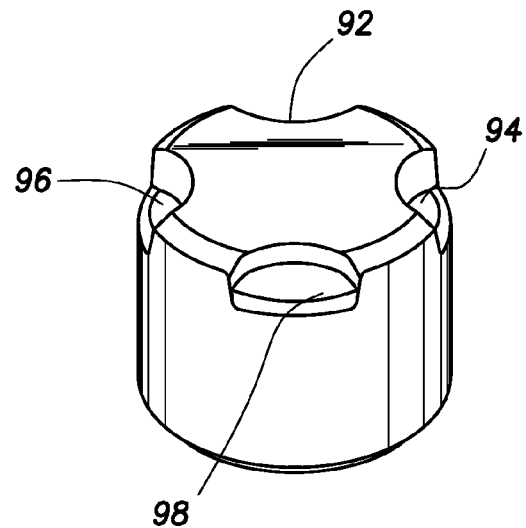
FIG. 3C provides a perspective view of the cap of FIG. 3A.
Figure 3B:
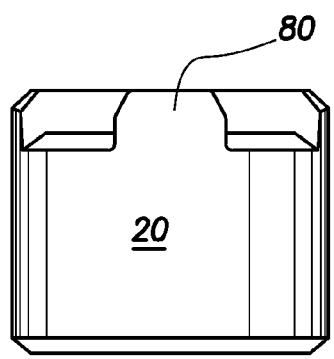
FIG. 3B provides a side view of the cap of FIG. 3A.

Referring now FIGS. 3A, 3B, and 3C, the cap 20 includes the insertion portion 80. In accordance with one aspect of the present invention, the insertion portion 80 defines four channels or cut-outs 92, 94, 96 and 98. Each cut-out has a near-crescent shape, as shown. However, the cut-outs 92, 94, 96, and 98 may have any suitable shape that facilitates fitting of the cap 20 into the open end 60, such as a polygonal shape. As shown, the insertion portion 80 of the cap 20 includes a circumferential annular beveled ridge.

In some instances, the cap 20 that is secured to the end of the housing 50 may be covered by an over-cap component. The over-cap component may be fabricated from a variety of materials, such as any of the materials employed for the carrier component. The over-cap may be fabricated from an opaque material so as to hide the presence of a device 40 as well as prevent contact with the surrounding during packaging and handling. The over-cap component may be elastomeric, for example to provide for a secure fit over the cap that is in sealing relation with the carrier component.

Figure 4:
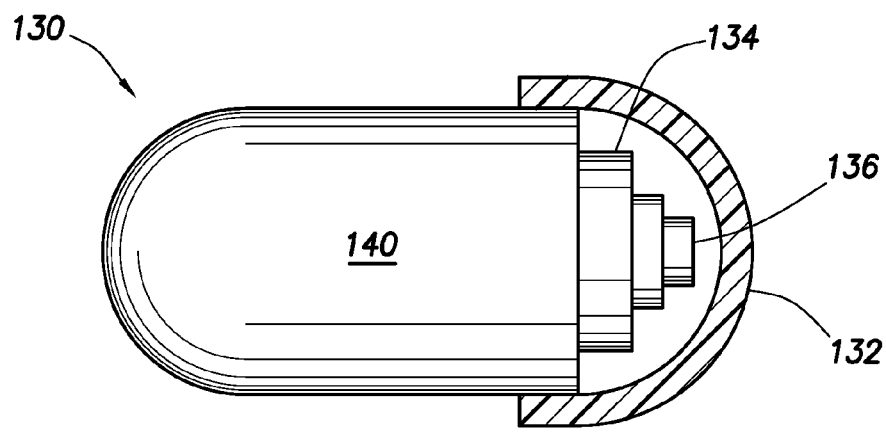
FIG. 4 provides a cross-sectional view of a pharmaceutical dosage with an over-cap according to the present invention.

Referring now to FIG. 4, in accordance with another aspect of the present invention a pharmaceutical dosage system 130 includes an over-cap 132. The pharmaceutical dosage system 130 includes a carrier component 140 sealed with a cap 134. The cap 134 includes a device 136, such as a current signature production device or IEM, on an outer surface thereof. Positioned over cap 134 is the over-cap 132. The over-cap 132 is secured to the carrier component 140 as shown; this prevents contact between the device 136 and conducting fluid once the pharmaceutical dosage system 130 is ingested. Once the over-cap 132 is released from the carrier component 140, the device 136 comes into contact with the surrounding environment and if that environment includes a conducting fluid, such as stomach fluid, then the device 136 is activated and produces a current signature that can be detected and decoded to retrieve information.

Where desired, the methods of preparing the dosage delivery system may further include preparing placebo pharmaceutical dosages. Placebo pharmaceutical dosages may be prepared in a manner analogous to the preparation of dosages that include a pharmaceutically active agent, with the exception that a pharmaceutically active agent is not placed inside of a carrier component. Instead, a vehicle composition that lacks an active agent, for example as described above, is placed inside of the carrier component and then sealed with the cap. Methods where placebo dosages are prepared include methods in which the pharmaceutical dosages are to be employed in clinical trials.

In accordance with yet another aspect of the present invention, the methods of preparing a dosage delivery system may further include preparing dosages having a device within the carrier, e.g., either alone or in combination with a filler. Such aspects may facilitate, among other applications, marking of an ingestion event of the dosage delivery system via production of a unique current signature.

In accordance with another aspect of the present invention, two different pharmaceutical agents may be placed within the housing 50 and separated by a filler composition. This physical separation is beneficial in instances where to different pharmaceutical agents must be mixed in solution to become active. Thus, as the housing 50 is dissolved, the two separate pharmaceutical agents are released into the surrounding fluid, such as the stomach fluid. This causes the two previously separated pharmaceutical agents to come into contact and combine, thereby allowing accurate delivery and combination of two different pharmaceutical agents at a target site.

Aspects of the invention further include methods of using the pharmaceutical dosages that are produced according to methods as described above. Generally, methods of the invention will include administering one or more pharmaceutical dosages to a subject, for example by having a subject ingest a pharmaceutical dosage of the invention. The dosages may be administered to a variety of different types of subjects. Generally such subjects are "mammals" or "mammalian," where these terms are used broadly to describe organisms which are within the class mammalia, including the orders carnivore (for example dogs and cats), rodentia (for example mice, guinea pigs, and rats), and primates (for example humans, chimpanzees, and monkeys). Following ingestion, a unique current signature is produced by an IEM and detected, for example with a receiver, such as described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753; U.S. patent application Ser. No. 61/251,088 filed Oct. 13, 2009; and PCT patent application serial no. PCT/US2009/068128 filed Dec. 15, 2009, each of the disclosures of which is herein incorporated by reference.

Methods of preparing pharmaceutical dosages and administering the same to subjects, for example as described above, find use in a variety of different applications. One application of interest is the use of the identifiers of the dosages as IEMs. Pharmaceutical dosages of the invention can be used in both therapeutic and non-therapeutic applications, such as reviewed in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753; the disclosures of which are herein incorporated by reference.

Applications of interest include automatic detection and identification of pharmaceutical agents actually delivered into the body, as may be done in: (1) monitoring patient adherence with prescribed therapeutic regimens; (2) tailoring therapeutic regimens based on patient adherence; (3) monitoring patient adherence in clinical trials; (4) monitoring usage of controlled substances; and the like. Each of these different illustrative applications is reviewed in greater detail in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753; the disclosures of which are herein incorporated by reference.

In certain embodiments, the methods of making pharmaceutical dosages of the invention are employed in clinical trials. Clinical trials in which the methods and compositions of the invention include multi-patient studies that are conducted to allow safety and efficacy data to be collected for a new pharmaceutically active agent. Examples of clinical trials include studies where investigators enroll healthy volunteers and/or patients into small pilot studies initially, followed by larger scale studies in patients that often compare the new product with a currently prescribed treatment. Furthermore, clinical trials may also compare the active agent of interest with a placebo composition. In these instances, placebos may be produced in a manner analogous to the methods of producing pharmaceutical dosages of the invention, with the only difference being that a pharmaceutically active agent composition is not sealed the carrier component. As positive safety and efficacy data are gathered in a given clinical trial, the number of patients may be increased. Clinical trials can vary in size from a single center in one country to multi-center trials in multiple countries.

Performing clinical trials with pharmaceutical dosages prepared according to the invention provides a number of advantages. One advantage is that the clinical trial manager (the entity who is running the clinical trial) can use standard carrier components and caps and customize these as needed with a given pharmaceutically active agent composition.

Also provided are systems that include one more pharmaceutical dosages of the invention, as described above. In addition to the pharmaceutical dosages of the invention, the systems may include body-associated signal receivers for detecting changes in voltage potential that represent receiving encoded information from a pharmaceutical dosage carrier in accordance with the teaching of the present invention. Body-associated receivers of interest include those described in PCT/US2008/052845 published as WO/2008/095183 and PCT/US2006/016370 published as WO/2006/116718; the disclosures of which are herein incorporated by reference. As described in these incorporated applications, the receivers may be implanted or on a body surface of a patient. The systems may further include additional data relay and/or processing components, such as wireless communication devices (such as cell phones); data processors as may be found in computers and information systems, etc.

Also provided are kits for practicing the subject methods. Kits may include one or more carrier components and associated caps of the invention, as described above. The carrier components and associated caps of the kits will be equipped to receive a dosage amount of one or more pharmaceutically active agent compositions to be sealed therein; such as pharmaceutically active agent compositions being provided separately from the instant kits. Where desired, the kits may also include one or more filler compositions. A given kit may include sufficient carrier components and caps to make 1 or more, including 5 or more, such as 50 or more, 100 or more, 1000 or more, 5000 or more, or 10000 or more pharmaceutical dosages.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. Where desired, the components of the kit are packaged in a kit containment element to make a single, easily handled unit, where the kit containment element may be a box or analogous structure and may or may not be an airtight container.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Certain ranges have been presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A pharmaceutical delivery system for tracking delivery parameters, the system comprising:
   a carrier housing having a closed end and an open end, wherein the carrier housing defines a cavity;
   a pharmaceutical agent positioned within the cavity of the carrier housing;
   a cap comprising a top end and a bottom end, wherein the bottom end includes a sealing portion that is in physical communication with the open end of the carrier housing to seal the cavity containing the pharmaceutical agent; and
   a device associated with the system, wherein the device produces an identifiable current signature for communicating information, wherein the device is secured to a top portion of the cap such that the device is able to come into contact with the surrounding environment as the carrier housing comes into contact with the surrounding environment.

2. The system of claim 1, wherein the sealing portion defines at least one channel that allows the cap to be pressure fitted into the open end of the carrier housing.

3. The system of claim 1, wherein the sealing portion is secured to the open end of the carrier housing an adhesive.

4. The system of claim 1, wherein the device comprises:
   a frame;
   a conductance control module secured within the frame for producing the identifiable current signature representing the information;
   a first material secured to the frame and electrically coupled to the conductance control module; and
   a second material secured to the frame and electrically coupled to the conductance control module,
   wherein the first material and the second material are separated by a non-conducting material and selected to produce a voltage potential when in contact with a conducting fluid.

5. A pharmaceutical carrier comprising:
   a housing that defines a cavity, wherein the housing includes an open end and a closed end;
   an apparatus positioned within the cavity of the housing for altering the buoyancy of the carrier;
   a cap comprising a top end and a bottom end, wherein the bottom end defines at least one channel for fitting the cap into the open end of the housing to seal the content of the cavity; and
   a current control device secured to the cap and for producing a unique current signature, wherein the current control device comprises:
   a conductance control module secured within a frame for producing an identifiable current signature; and
   a partial power source comprising a first material and a second material insulated from one another and each of the first material and the second material electrically coupled to the conductance control module, wherein the first material and the second material are secured to the frame.

6. The carrier of claim 5, wherein the partial power source of the current control device produces a voltage potential when the first material and the second material are electrically coupled through a conducting fluid in contact therewith and the voltage potential is used to activate the conductance control module to produce the identifiable current signature.

7. The carrier of claim 6, wherein the current control device is secured to the top end of the cap such that the current control device comes into contact with the conducting fluid at about the same time that the housing comes into contact with the conducting fluid and, hence, the current control device is activated upon contact with the conducting fluid.

8. The carrier of claim 6, wherein the current control device is secured to the top end of the cap and wherein the carrier further comprises an over-cap positioned over the top end of the cap, such that the over-cap prevents contact of the conducting fluid with the current control device until the over-cap dissolves, which causes a delay between the time of introduction of the carrier to the environment and activation of the conductance control module and thereby delaying generation of the identifiable current signature.

9. The carrier of claim 6, wherein the current control device is secured to the bottom end of the cap such that the current control device comes into contact with the surrounding environment after the cap is separated from the housing thereby delaying the current control device from producing the identifiable current signature.

10. The carrier of claim 5, wherein the cap includes a tapered portion at the bottom end and the housing includes a tapered portion at the open end such that the tapered portions are male-female mated and glued together thereby causing the cap to be secured into the open end of the housing to seal the cavity.

11. The carrier of claim 5, wherein the cap is mechanically fitted to the open end of the housing to seal the cavity of the housing.

12. The carrier of claim 5 further comprising a pharmaceutical agent positioned within the cavity of the housing.

13. The carrier of claim 5, wherein the apparatus has a composition that imparts to the device a density that is greater than stomach fluid.

14. An ingestible carrier for providing information associated with the ingestion of a pharmaceutical product, the carrier comprising:
   a dissolvable casing that defines a cavity, wherein the casing includes an open end and a closed end and the pharmaceutical product is positionable within the cavity defined by the casing;
   a cap comprising a top end and a bottom end that includes a securing portion, wherein the securing portion defines a plurality of channels that allow for insertion of the cap into the open end of the casing; and
   a current signature-production device associated with the carrier for producing a current signature that represents the information associated with the ingestion of the pharmaceutical product, wherein the device comprises:
   a frame;
   a conductance control module secured to the frame for producing the current signature representing the information; and
   a partial power source comprising a first material and a second material each electrically coupled to the conductance control module, wherein the first material and the second material are secured to the frame and separated by a non-conducting material and wherein the partial power source produces a voltage potential when the first material and the second material are electrically coupled through a conducting fluid in contact therewith and the voltage potential activates the conductance control module and hence the device.

15. The carrier of claim 14, wherein the device is secured to the top end of the cap such that the device contacts the conducting fluid at about the same time that the casing contacts the conducting fluid.

16. The carrier of claim 14, wherein the device is positioned on the top end of the cap and wherein the carrier further comprises an over-cap positioned around the cap and secured to the cap, such that the over-cap causes a delay in activation of the device by delaying contact between the device and the conducting fluid and, hence, a delay in production of the current signature.

17. The carrier of claim 14, wherein the device is secured to a bottom of the securing end such that the device comes into contact with the conducting fluid after the casing is dissolved to the point where the cap is released thereby causing a delay in producing the current signature.

18. The carrier of claim 14, wherein the device is placed within the cavity defined by the casing.

19. The carrier of claim 14, wherein the carrier further comprises a filler composition positioned within the cavity defined by the casing to prevent movement of the pharmaceutical product and the device within the cavity defined by the casing.

20. The carrier of claim 14, further comprising a buoyancy altering apparatus positioned within the cavity defined by the casing.

21. The carrier of claim 14, wherein the securing portion is glued into the open end of the casing.

22. The carrier of claim 14, wherein the securing portion is mechanically secured the open end of the casing.

23. The carrier of claim 14, wherein the securing portion is pressure fitted to the open end of the casing.

24. A pharmaceutical delivery system for tracking delivery parameters, the system comprising:
   a carrier housing having a closed end and an open end, wherein the carrier housing defines a cavity;
   a pharmaceutical agent positioned within the cavity of the carrier housing;
   a cap comprising a top end and a bottom end, wherein the bottom end includes a sealing portion that is in physical communication with the open end of the carrier housing to seal the cavity containing the pharmaceutical agent; and
   a device associated with the system, wherein the device produces an identifiable current signature for communicating information, wherein the sealing portion defines at least one channel that allows the cap to be pressure fitted into the open end of the carrier housing.

25. A pharmaceutical delivery system for tracking delivery parameters, the system comprising:
   a carrier housing having a closed end and an open end, wherein the carrier housing defines a cavity;
   a pharmaceutical agent positioned within the cavity of the carrier housing;
   a cap comprising a top end and a bottom end, wherein the bottom end includes a sealing portion that is in physical communication with the open end of the carrier housing to seal the cavity containing the pharmaceutical agent; and
   a device associated with the system, wherein the device produces an identifiable current signature for communicating information, wherein the sealing portion is secured to the open end of the carrier housing an adhesive.

26. A pharmaceutical delivery system for tracking delivery parameters, the system comprising:
   a carrier housing having a closed end and an open end, wherein the carrier housing defines a cavity;
   a pharmaceutical agent positioned within the cavity of the carrier housing;
   a cap comprising a top end and a bottom end, wherein the bottom end includes a sealing portion that is in physical communication with the open end of the carrier housing to seal the cavity containing the pharmaceutical agent; and
   a device associated with the system, wherein the device produces an identifiable current signature for communicating information, wherein the device comprises:
      a frame;
      a conductance control module secured within the frame for producing the identifiable current signature representing the information;
      a first material secured to the frame and electrically coupled to the conductance control module; and
      a second material secured to the frame and electrically coupled to the conductance control module,
   wherein the first material and the second material are separated by a non-conducting material and selected to produce a voltage potential when in contact with a conducting fluid.

* * * * *